(12) United States Patent
McIntosh et al.

(10) Patent No.: US 9,974,841 B2
(45) Date of Patent: May 22, 2018

(54) HIGH OSTEOCALCIN MICROCRYSTALLINE HYDROXYAPATITE FOR CALCIUM SUPPLEMENT

(71) Applicant: Waitaki Biosciences, Christchurch (NZ)

(72) Inventors: Craig Lachlan McIntosh, Christchurch (NZ); Susan Finderup, Christchurch (NZ); Harold Garthwaite, Christchurch (NZ)

(73) Assignee: WAITAKI BIOSCIENCES, Christchurch (NZ)

( * ) Notice: Subject to any disclaimer, the term of this patent is extended or adjusted under 35 U.S.C. 154(b) by 0 days. days.

(21) Appl. No.: 14/916,695

(22) PCT Filed: Sep. 4, 2014

(86) PCT No.: PCT/IB2014/001732
§ 371 (c)(1),
(2) Date: Mar. 4, 2016

(87) PCT Pub. No.: WO2015/033211
PCT Pub. Date: Mar. 12, 2015

(65) Prior Publication Data
US 2016/0228517 A1 Aug. 11, 2016

Related U.S. Application Data

(60) Provisional application No. 61/874,324, filed on Sep. 5, 2013.

(51) Int. Cl.
| | | |
|---|---|---|
| *A61K 38/39* | (2006.01) |
| *A23L 33/16* | (2016.01) |
| *A61K 9/14* | (2006.01) |
| *A61K 33/42* | (2006.01) |
| *A23L 33/17* | (2016.01) |
| *A61K 35/32* | (2015.01) |

(52) U.S. Cl.
CPC .............. *A61K 38/39* (2013.01); *A23L 33/16* (2016.08); *A23L 33/17* (2016.08); *A61K 9/14* (2013.01); *A61K 33/42* (2013.01); *A23V 2002/00* (2013.01); *A61K 35/32* (2013.01)

(58) Field of Classification Search
None
See application file for complete search history.

(56) References Cited

U.S. PATENT DOCUMENTS

| | | |
|---|---|---|
| 4,919,931 A | 4/1990 | Rosenberg nee Goldner |
| 5,942,502 A | 8/1999 | DeLuca et al. |
| 7,029,703 B2 | 4/2006 | Krumhar et al. |
| 2003/0059481 A1 | 3/2003 | Krumhar et al. |
| 2005/0037109 A1 | 2/2005 | Soerensen et al. |
| 2007/0254040 A1 | 11/2007 | Scaffidi |
| 2009/0238930 A1 | 9/2009 | Sathivel |

FOREIGN PATENT DOCUMENTS

CN 1843502 A * 10/2006

OTHER PUBLICATIONS

English Translation of CN1843502 retrieved from Espacenet on Aug. 24, 2017.*
International Search Report issued in PCT/IB2014/001732, dated Dec. 18, 2014.
International Preliminary Report on Patentability for PCT/IB2014/001732, dated Oct. 2, 2015.
Bolland M. J. et al., Calcium supplements with or without vitamin D and risk of cardiovascular events: reanalysis of the Women's Health initiative limited access dataset and meta-analysis. *British Medical Journal*, 2011; 342:d2040 (9 pages).
Bolland M. J. et al., Vascular events in healthy older women receiving calcium supplementation: randomised controlled trial. *British Medical Journal*, 2008; 336:262-266.
Castelo-Branco C., et al., Efficacy of ossein hydroxyapatite complex with calcium carbonate to prevent bone loss: a meta-analysis. *Menopause*, 2009; 16(5):984-991.
Deroisy R. et al., Acute changes in serum calcium and parathyroid hormone circulating levels induced by the oral intake of five currently available calcium salts in healthy male volunteers. *Clinical Rheumatology*, 1997; 16(3):249-253.
Michaelsson K. et al., Long term calcium intake and rates of all cause and cardiovascular mortality: community prospective longitudinal cohort study. *British Medical Journal*, 2013; 346:f228 (13 pages).
Pelayo I. et al., Raloxifene plus ossein-hydroxyapatite compound versus raloxifene plus calcium carbonate to control bone loss in postmenopausal women: a randomized trial. *Menopause*, 2008; 15(6) (7 pages).
Reid I. R. The acute biochemical effects of four proprietary calcium preparations. *Aust NZ J Med.*, 1986; 16(2):193-197.
Ruegsegger P. et al., Comparison of the treatment effects of ossein-hydroxyapatite compound and calcium carbonate in osteoporotic females. *Osteoporosis International*, 1995; 5:30-34.
Sambrook, P. N. et al., Does increased sunlight exposure work as a strategy to improve vitamin D status in the elderly: a cluster randomised controlled trial. *Osteoporosis International*, Mar. 3, 2011; 23(2):615-24.
Stepan, J. J. et al., Quantitation of growth factors in ossein-mineral-compound. *Life Sciences*, 1991; 49(13):PL79-PL84.

* cited by examiner

*Primary Examiner* — Jessica Worsham
(74) *Attorney, Agent, or Firm* — Venable LLP; Keith G. Haddaway; Kerri M. Patterson

(57) ABSTRACT

An improved manufacturing process produces microcrystalline hydroxyapatrte with sustained gradual calcium release that avoids spiking in blood calcium levels. Although the improved material did not cause significant elevation of blood calcium, it was just as effective in promoting bone mineralization as conventional calcium supplements. In addition, the material has much higher levels of bone growth factors as compared to prior hydroxyapatite products.

12 Claims, 5 Drawing Sheets

HIGH OSTEOCALCIN MICROCRYSTALLINE HYDROXYAPATITE FOR CALCIUM SUPPLEMENT

CROSS-REFERENCE TO RELATED APPLICATIONS

This application is a U.S. National Phase of International Application No. PCT/IB2014/001732, filed Sep. 4, 2014, which claims priority to U.S. Provisional Patent Application No. 61/874,324, filed Sep. 5, 2013, the entire contents of each are incorporated by reference herein.

BACKGROUND OF THE INVENTION

Area of the Art

The current invention is in the area of nutrients and dietary supplements and more specifically deals with a novel calcium supplement.

Description of the Background of the Invention

It seems that everywhere one turns in a supermarket one finds food products prominently labeled "With Calcium." A visit to the dietary supplement aisle shows a plethora of calcium supplements. It seems clear that there must be a worldwide crisis in dietary calcium. Certainly, calcium is extremely important in cellular biology. Many important cellular processes are controlled or modulated by calcium ions. Generally, the most important metal ions for cellular physiology are calcium, sodium and potassium. Perhaps not unsurprisingly, these are also amongst the most abundant metal ions in sea water.

In humans calcium serves not only as a vital ion in cellular processes but as a building material for the skeleton. Bone consists of about 50-70% mineral—almost entirely calcium phosphate in the form of microcrystalline hydroxyapatite (MCHA). Most of the remainder of bone is a protein matrix (primarily collagen) secreted by the bone cells. The active bone cells mineralize the collagen matrix as well as constantly remodel the bone by withdrawing and redepositing calcium. The skeleton serves as a calcium depot with the body constantly withdrawing calcium to maintain the correct level of cellular calcium—that withdrawal process is the source of the apparent dietary calcium crisis. As long as dietary calcium is adequate, the calcium depot remains filled and structural integrity of the bone is maintained.

Dairy products are excellent calcium sources as are many fruits and vegetable because calcium also plays a structural role in the "skeletons" of plants. However, as people age, they often become lactose intolerant and shun dairy products because of the untoward digestive repercussions to consumption of dairy products. Generally, human diets are also deficient in fruits and vegetables so that real shortages of dietary calcium may well exist. To compound the problem vitamin D is required to properly absorb available dietary calcium, and vitamin D deficiencies are common particularly in the elderly. Moreover, hormonal changes due to aging, particularly in postmenopausal females, militate against proper bone building. The result is osteoporosis with its danger of debilitating fractures.

In the elderly a fracture—particularly a hip fracture—due to osteoporosis may well signal the end of health and productivity and result in a rapid downward spiral in the individual's overall health. So there really is a crisis in dietary calcium. As the population lives longer, osteoporosis becomes more and more of a problem. The general response has been to supplement the diet with more and more calcium in an effort to prevent efflux of calcium from the skeleton. In addition, various drugs are used in an effort to either stimulate bone formation or inhibit bone resorption. On the dietary front the most common form of added calcium is calcium carbonate (limestone) although calcium citrate is also a fairly popular source of added dietary calcium. To a much lesser extent calcium phosphate (hydroxyapatite) has also been used as a dietary calcium supplement.

Until recently, the bioavailability—that is, rapid absorbability—was considered the key factor in selection of calcium supplements. But then a number of studies began to uncover an unanticipated correlation between consumption of calcium supplements and coronary heart diseases. These controversial results have been perplexing because other studies have shown that adequate levels of dietary calcium are often heart protective. In addition, there is some evidence that inhabitants of areas with "hard" drinking water (water high in calcium) also show improved coronary health. So there appears to be some problem with consuming calcium supplements as opposed to a normal calcium-rich diet. There are a number of possible factors involved. Coronary infarctions result from arterial blockages due to plaque formation. Abnormal platelet aggregation is usually implicated in plaque formation and diseased arteries often become stiff with calcium deposits (so called hardening of the arteries). It is known that calcium ions promote platelet aggregation as well as blood coagulation. Perhaps supplements result in abnormally high blood calcium levels that promote platelet aggregation and calcium deposition. Another factor is that cardiomyocytes (heart muscles cells) require extracellular calcium for contraction—perhaps if the blood calcium levels are abnormally high, contraction is affected. In any case, it is clear that osteoporosis cannot be safely treated or prevented by simply mega-dosing on calcium supplements.

SUMMARY OF THE INVENTION

Calcium supplements are believed to be vital to avoiding osteoporosis and bone fractures in aging individuals. Generally, the diets of middle age and older adults lacks sufficient calcium to ensure long-term bone health. Many popular foods lack adequate calcium and lactose intolerance causes many adults to eschew dairy products. The serious problems with bone fractures in the middle age and older population have resulted in a boom in calcium supplements. The most common supplement is calcium carbonate followed by other calcium salts such as calcium citrate and even calcium gluconate.

Until recently, the goal of calcium supplements has been to ensure rapid dissolution and absorption of the added calcium. However, some meta-analyses have detected what appears to be increased cardiac disease in some patients receiving calcium supplements. Although this finding is controversial, it is prudent to provide calcium supplements that more closely mirror the effects of normal calcium rich diets.

Dietary calcium appears to be slowly absorbed during the digestive process and does not result in any changes in the blood level of ionized calcium. On the other hand, popular calcium supplements such as calcium carbonate are more rapidly absorbed and result in detectable elevation ("spiking") of blood calcium levels.

Traditionally, calcium phosphate (hydroxyapatite) isolated from bones has been used as a calcium supplement although it has fallen out of favor for not being as "bioavailable" as materials such as calcium carbonate. We have developed an improved process for manufacturing microcrystalline hydroxyapatite from bones. The improved material supports bone mineralization without causing any spiking of blood calcium levels because the calcium is released and absorbed over a relatively long time following ingestion. Furthermore, the improved material has a higher level of bone growth factors. These promote the differentiation of osteoblasts in culture. It is believed that this calcium source will promote bone mineralization while avoiding any negative cardiac effects due to spiking of blood calcium levels.

DETAILED DESCRIPTION OF THE INVENTION

Figure 1:
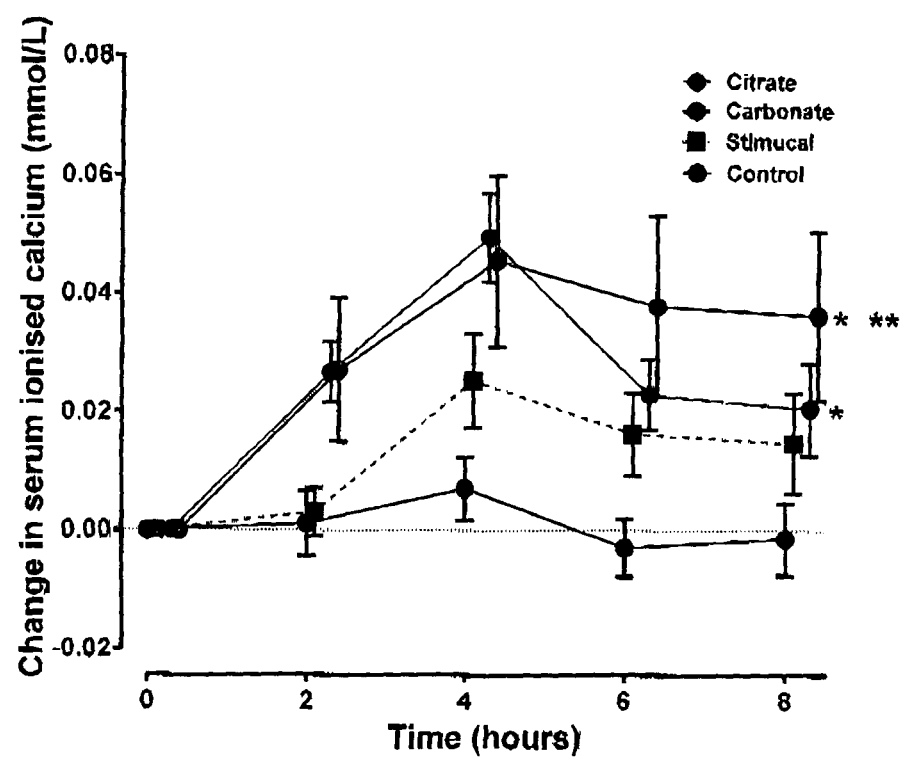
FIG. 1 is a graph comparing the blood levels of ionized calcium from two different hydroxyapatite preparations to calcium levels provide by other calcium supplements.

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide an improved calcium hydroxyapatite calcium supplement that offers a solution to the problem of possible negative effects of calcium supplements.

Because it seems unlikely that "natural" dietary calcium is fundamentally different from supplemental calcium, it appears that the apparent cardiac problem may be related to the rate of calcium absorption and excretion. A normal well-balanced diet contains sufficient calcium, but that calcium is generally bound to other food components. For example, much of the calcium available in plant material is reversibly bound to certain carbohydrates. During digestion of the food this calcium is gradually released and absorbed mostly in the small intestine. As calcium is being added to the blood stream, it is being simultaneously removed for cellular use and for calcification of bone matrix. Natural homeostatic mechanisms keep the blood concentration of calcium constant at approximately 1 mM which is approximately 10,000 times the normal cellular concentration of calcium. If the diet is supplying excess calcium, calcium is excreted through the kidneys to maintain the 1 mM concentration. However, when large amounts of readily ionized calcium sources are ingested, the results might be different. Ingesting several tablets of calcium carbonate or calcium citrate probably causes a much higher level of ionized calcium to enter the intestine than the amount provided by a normal diet.

In fact, recent tests have shown that when usual supplement amounts of either calcium carbonate or calcium citrate are consumed, blood levels of calcium spike above the normal 1 mM concentration demonstrating that the normal homeostatic control of calcium concentration is being overwhelmed. Surprisingly, this spike continues for around eight hours after ingestion of the supplement. It will be appreciated that ensuring an optimum level of calcium should favor bone mineralization. Ideally, dietary intake should be sufficient to maintain the 1 mM blood calcium concentration even though cellular processes and bone mineralization are constantly withdrawing calcium from the blood. If insufficient calcium is supplied to maintain the blood calcium levels, cellular processes take precedence and calcium is withdrawn from the bone "bank" to maintain adequate blood levels of calcium. A long-term calcium deficit will result in bone demineralization—osteopenia and osteoporosis. But there is no reason to suppose that providing so much excess calcium so as to override homeostasis necessarily increases the rate of bone mineralization. Clearly, maintaining the blood concentration at normal levels, discourages withdrawal of calcium from the bones, but the process of bone mineralization is controlled by a number of factors besides availability of free calcium. Moreover, now that we understand that chronically high calcium concentrations may promote cardiac problems, the focus of calcium supplementation necessarily changes. The new goal is to constantly provide sufficient calcium so that calcium is never withdrawn from the bones to maintain proper calcium blood concentration while ensuring that calcium is supplied at a sufficiently slow rate that any excess calcium can be excreted without causing significant long-term elevation of calcium blood concentration.

Since it is clear that conventional calcium supplements are absorbed too rapidly, there seems at least two ways that their use might be continued safely. One possibility might be to administer them in small doses spread out over the entire day (and night), However, this might make it difficult to maintain adequate calcium levels if the basic diet is strongly calcium deficient. The second solution would be to use current controlled release technology to allow a single dose of supplement to release calcium slowly over a much more extended period of time. Such an approach is certainly feasible although it is likely to add bulk (to already bulky calcium supplements) as well as cost. Fortunately, the present inventors have discovered an additional way to provide effective calcium supplementation without the danger of excessive concentrations of blood calcium.

For some time microcrystalline hydroxyapatite (MCHA) manufactured from animal bones has been used as a slightly unconventional calcium supplement. Considering that bone mineral is largely calcium phosphate in the form of hydroxyapatite, it seems logical to use MCHA as a source of bone calcium. However, there can be some difficulty in purifying MCHA from native bones because there is considerable excess protein and lipid that must be removed to provide a stable as well as readily digestible product. As might be imagined there is considerable variation in the process parameters for making an MCHA product. In a study intended to compare MCHA to conventional calcium supplements, the inventors analyzed MCHA produced using varied protocols. They were surprised to discover that depending on how the MCHA is manufactured, its rate of bioabsorption changes quite dramatically. After considerable experimentation, the inventors developed the current product which was then compared to calcium carbonate and calcium citrate in both an absorption (measured by blood calcium concentration) and a bone mineralization/density study.

Blood calcium concentration studies showed that ingestion of calcium citrate versus ingestion of calcium carbonate were not statistically significantly different; both calcium sources resulted in long-term (ca. 8 hour) spiking of blood calcium concentration. On the otherhand, the preferred inventive MCHA was not statistically significantly different from the calcium-free placebo. That is, following administration of the MCHA the blood calcium concentration did not increase significantly. However, it must be kept in mind that the blood calcium concentration is maintained by withdrawing calcium from the bones if the dietary supply is insufficient. The fact that the MCHA was not statistically significant from the placebo does not necessarily mean that no calcium was being absorbed; it means only that calcium was being absorbed at a rate slow enough to prevent spiking in the blood calcium concentration.

In FIG. 1 the blood levels of ionized calcium of two different MHCA preparations (see below for preparation details) are compared to blood calcium levels provided by other calcium supplements. The figure shows that both calcium carbonate and calcium citrate cause a rapid increase in ionized blood calcium. After 6 hours citrate begins to decline indicating that most of it has been absorbed. MHCA 1 (the first preparation described has no effect on ionized calcium level for over 2 hours and then only a slight effect which is not statistically significantly (asterisks) different than the control (no calcium supplement). MHCA 2 (the finer particle preparation) releases somewhat more calcium than MHCA 1, It will be apparent to one of skill in the art that should it be desired to release calcium even more slowly, the particle size of the MCHA can be easily increased.

Although MCHA does not result in significant spiking of ionized calcium, over a 90 day study administration of MCHA showed essentially no differences in factors indicative of bone formation (PTH [parathyroid hormone], CTX [beta-carboxy-terminal cross-linking telopeptide of type I collagen] and P1NP [type 1 procollagen amino-terminal-propeptide] as compared to spiking calcium supplements such as calcium carbonate and calcium citrate.

The impact of the calcium supplements (MHCA, carbonate and citrate) over the 90 day experimental duration on bone calcium level and other markers of bone mineralization and turnover were not statistically significantly different from each other whereas all were statistically significantly different from the calcium-free placebo. Therefore, the inventive MCHA provided as much effective calcium as the other supplements but did so without causing spiking of the blood calcium concentration. As detailed below MCHA is extracted from native bone and contains all or most of the bone matrix proteins. It seems likely that the hydroxyapatite was released for absorption only after enzymatic digestion of these proteins. That is, the MCHA is inherently a time release product and the rate of this release can be manipulated by the process used to manufacture the MCHA.

The process to manufacture MCHA is fairly straightforward. It differs from prior art processes in that temperature and pH are controlled to avoid denaturing growth factors present in the bone protein matrix. Most prior art processes also employed organic solvents to defat the bone—these also can contribute to denaturation of growth factors.

Step 1) Raw Material Procurement

Leg bone, (diaphysis only from the radius, femur and tibia) of prime bovine of 30 months or less age is sourced from export licensed meat processing plants. Bovines are pre and post mortem inspected and cleared as fit for human consumption. Bovine bone is block frozen to below −12° C. in approved food contact grade cartons.

Frozen material is received from the collection plant with an authorized transfer certificate.

Documentation and frozen product is checked and then removed from the cartons.

Step 2) Frozen bone is "minced" to reduce particle size

Step 3) Temperature Controlled Digestion Process.

Product is immersed in potable water to achieve a target temperature of 60° C.-70° C. and pH is adjusted to achieve a target of 8.5-8.7

Protease (alcalase) is added to remove non-active tissues and fat.

Step 4) Drying and Milling

The product slurry is dried under low temperature vacuum, or freeze-dried, for not more than 24 hours until not more than 5% moisture remains Product is unloaded into sealed bags Product is milled into a fine powder until the required particle size distribution of not more than 30% smaller than 250 micron and not less than 90% smaller than 850 micron is achieved (30% Maximum through US Standard 80 mesh screen and 90% Minimum through 20 US Standard mesh screen).

Packed into foil laminate bags inside cardboard carton,

Samples are taken for microbial and chemical testing

The final size distribution of the particles is a product of the degree of mechanical processing and the various mesh sizes used to sieve the product. The starting bone is "minced" with a mincer/grinder (Bellmore Engineering, Christchurch, NZ) using a 10 mm hole plate. Product milling is done with a model 40B Impact Mill (Chenggan Drying of Jiangsu, China) using a 1.5 mm mill screen and a 1 mm sieve screen. The mill was operated at the 19 amp speed setting.

The end product has the following analysis:

| Analysis | Specification |
| --- | --- |
| Loss on drying (Moisture) %: | <5 |
| Fat %: | <1.5 |
| Protein (N × 6.25) %: | 24 to 28 |
| Ash (Residue on Ignition) %: | 65 to 75 |
| Calcium (Ca) % | 25 to 29 |
| Phosphorus (P) % | 10 to 13 |
| Calcium Hydroxyapatite %: | 60 to 72 |

In developing this manufacturing procedure the inventors considered the influence of overall composition and physical characteristics on the rate of calcium dissolution in vitro using the theory that in vitro dissolution would likely be related to in vivo calcium absorption. For these tests an aliquot of material to be tested was placed in 600 ml of 0.1M HCl in a Dissolution Tester manufactured by the TDTF Corporation of Jiangsu, China. The mixture was stirred at 150 RPM at a temperature of 37±0.5° C. with samples removed periodically. The samples were centrifuged to remove undissolved material and the supernatant was diluted with $NH_3/NH_4Cl$ buffer (pH 10) containing with eriochrome black T as an indicator and titrated to endpoint with 0.1 M EDTA, Under these conditions the eriochrome is red in the presence of calcium ions. When sufficient EDTA has been added to chelate all the calcium, the solution turns from red to blue and the amount of added EDTA can be used to calculate the original calcium on concentration.

Figure 2:
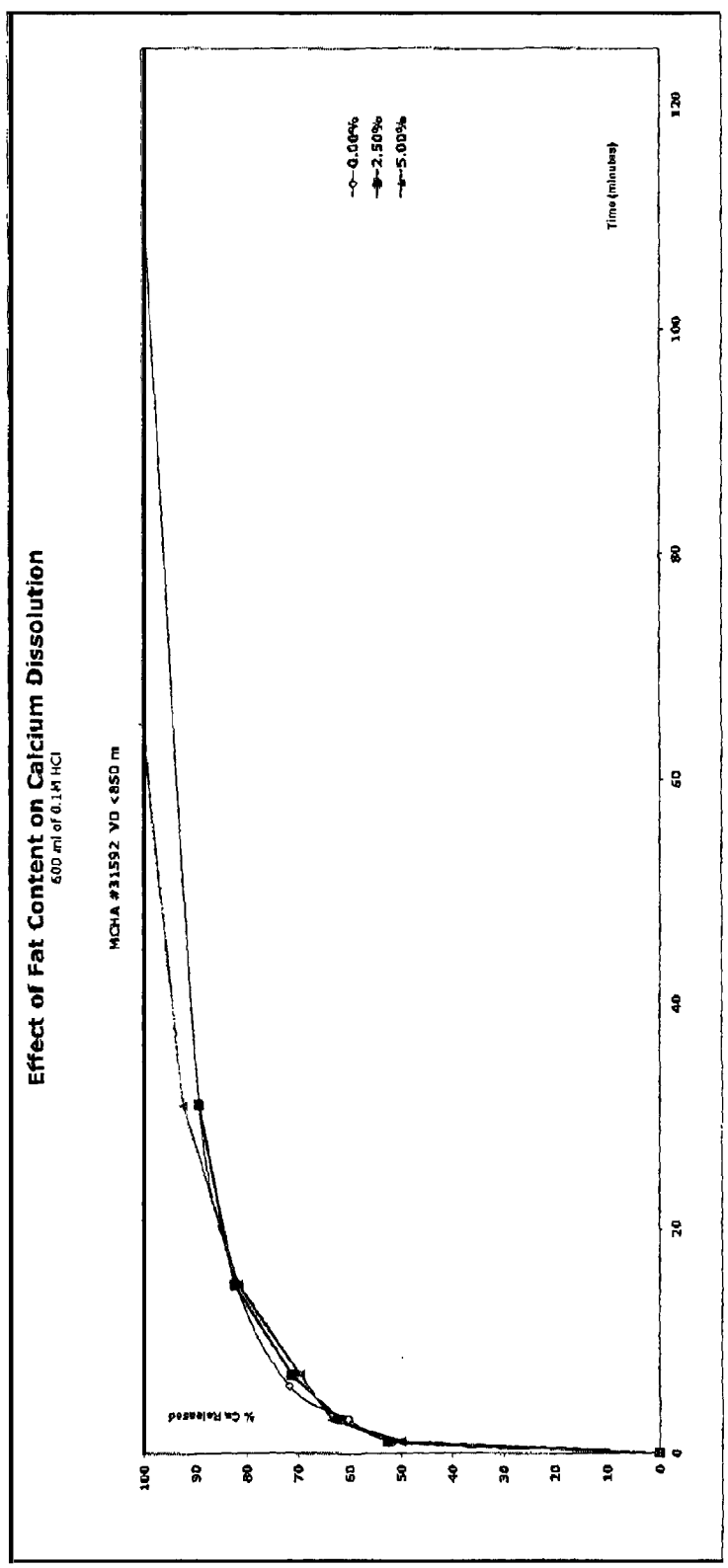
FIG. 2 is a graph showing the effect of fat content on calcium dissolution rate.
Figure 3:
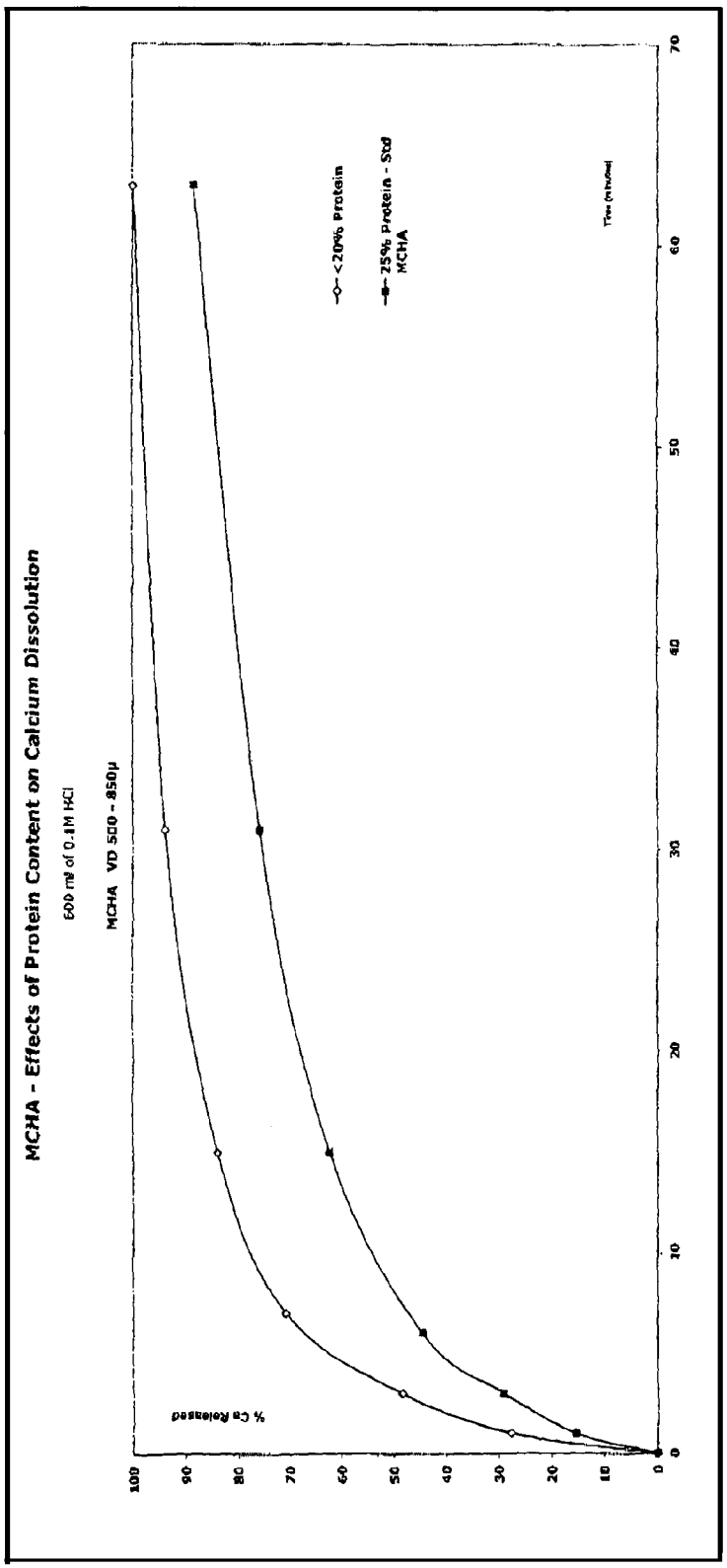
FIG. 3 is a graph showing the effect of protein content on calcium dissolution rates.

The current inventive process produced an MHCA containing more protein and less fat than prior art MHCA preparations while providing a high level of calcium. FIG. 2 shows dissolution results for 0.0%, 2.5% and 5.0% fat, increased fat content appears to correlate with more rapid dissolution of the calcium—a somewhat paradoxical result since fat is generally considered to slow the digestive processes. FIG. 3 shows the results of a similar experiment run on similar MHCA products that contained different concentrations of protein. The figure shows that a product containing 25% protein released calcium more slowly than one containing 20% protein. It seems likely that the current process preserves the protein (mostly collagen) matrix surrounding the hydroxyapatite and that the presence of this matrix slow the dissolution of the calcium.

The present process produces a product that has a different analysis than prior art MHCA products such as "OHC" which is produced according to U.S. Pat. No. 4,919,931. In terms of gross analysis, the present product has more calcium and phosphorous than OHC. The present product also has different particle size distribution than OHC.

The following tables demonstrate that particle distribution size is somewhat more complex than is indicated by the simple screen mesh specifications given in relation to the manufacturing process. The specification requires that more than 90% of the particles (on a weight basis) be smaller than 850 micrometers while not more than 30% of the particles (on a weight basis) be smaller than 250 micrometers. This specification does not define the actual particle size distribution of the preparation. The following table shows an actual screening test. Standard screens have a nominal square opening size, but because actual milled particles are usually elliptical or even somewhat irregular, the average particle size retained by the screen is somewhat larger than the screen opening size.

| Mesh | Opening (μm) | Measured (μm) | Wt. retained (g) | % retained | % cumulative |
| --- | --- | --- | --- | --- | --- |
| 18 | 1000 | 1100 | 0.00 g | 0.0% | 100.0% |
| 20 | 850 | 1000 | 0.5 g | 0.5% | 100.0% |
| 35 | 500 | 675 | 8.0 g | 7.7% | 99.5% |
| 50 | 300 | 400 | 57.0 g | 55.1% | 91.8% |
| 70 | 250 | 275 | 9.0 g | 8.7% | 36.7% |
| 80 | 180 | 215 | 10.0 g | 9.7% | 28% |
| 100 | 150 | 200 | 3.0 g | 2.9% | 18.4% |
| 140 | 106 | 128 | 5.0 g | 4.8% | 15.5% |
| 200 | 75 | 90.5 | 3.0 g | 2.9% | 10.6% |
| 270 | 53 | 64 | 3.0 g | 2.9% | 7.7% |
| (Pan) | | | 5.0 g | 4.8% | 4.8% |

The MHCA with the above screen profile is the same as "MHCA 1" in the clinical tests. This screening test shows that about 4.8% (by weight) of the material passes through a 270 mesh screen. This product meets the specification of less than 30% passing an 80 mesh (actually 18.4% passes) but the above shows the distribution of these very small particles with the majority (74%) being larger than a 270 mesh screen). In terms of large particles, the specification allows as much as 10% (by weight) to be larger than a 20 mesh screen. In fact only 0.5% of the particles are larger than 20 mesh and 0.0% are larger than an 18 mesh. Further 55.1% are retained by a 50 mesh screen and only 36.7% are retained by a 70 mesh which demonstrates a peak in the particle distribution. That is, 99.5% of the particles are smaller than 850 μm; 91.8% are smaller than 500 μm; 8.2 are larger than 500 μm; 28.0% are smaller than 250 μm; and 72.0% are greater than 250 μm. Another way of considering the size characteristics of such a heterogeneous powder is to compare the tapped (agitated to remove air) versus the untapped bulk density which in this case is 1.08 versus 1.13. Generally, the protein mesh surrounding the hydroxyapatite slows absorption of the calcium. Smaller particles digest faster (more surface area) so the calcium is more rapidly absorbed.

In perfecting the present embodiment of the product several different particle milling regimes were experimented with. It was demonstrated both in vitro and in vivo that particle size distribution alters the dissolution and the bioavailability of the calcium. The next table shows a preparation with a different particle size distribution produced by more extensive milling of the material. This material is the same as "MHCA 2" in the clinical tests.

| Mesh | Opening (μm) | Measured (μm) | Wt. retained (g) | % retained | % cumulative |
| --- | --- | --- | --- | --- | --- |
| 18 | 1000 | 1100 | 0.00 g | 0.0% | 100.0% |
| 20 | 850 | 1000 | 0.00 g | 0.0% | 100.0% |
| 35 | 500 | 675 | 0.00 g | 0.0% | 100.0% |
| 50 | 300 | 400 | 0.00 g | 0.0% | 100.0% |
| 70 | 250 | 275 | 0.00 g | 0.0% | 100.0% |
| 80 | 180 | 215 | 0.00 g | 0.0% | 100.0% |
| 100 | 150 | 200 | 2.0 g | 2.4% | 100.0% |
| 140 | 106 | 128 | 22.00 g | 25.9% | 97.6% |
| 200 | 75 | 90.5 | 18.00 g | 21.2% | 71.8% |
| 270 | 53 | 64 | 25.00 g | 29.4% | 50.6% |
| (Pan) | | | 18.00 g | 21.2% | 21.2% |

Here 100% of the particles are less than 180 μm with 97.6% less than 150 μm and 21.2% less than 53 μm (i.e., pass through a 270 mesh screen). As shown in the clinical tests this version of MHCA with smaller particles provides calcium more rapidly than MHCA 1, but still not nearly as rapidly as traditional calcium supplements. There may be a possibility of further optimizing the MHCA by creating a product having a particle profile somewhere between that of MHCA 1 and MHCA 2. If it is desired to release calcium even more slowly, then a product having a particle profile even large than MHCA 1 should be considered.

Figure 4:
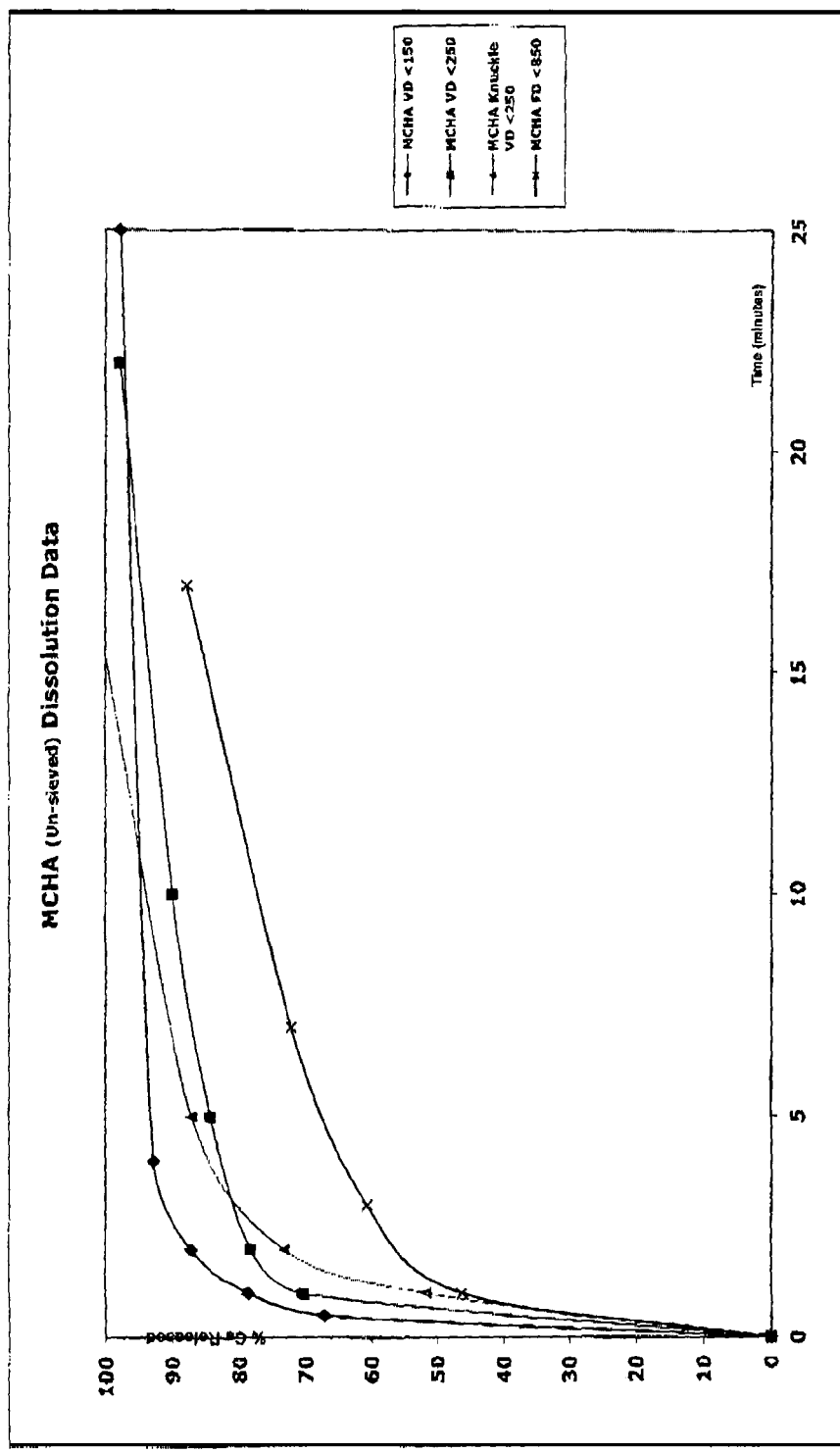
FIG. 4 is a graph showing the effects of particle size on dissolution rate.

FIG. 4 shows the test results of various particle size compositions using the in vitro dissolution test explained above. The figure demonstrates that maximum particle size and particle size distribution have a very significant effect on the rate of calcium dissolution. The following graph compared material that has been processed to provide different maximum particle sizes—namely <150 μm, <250 μm, and <850 μm. The rate of dissolution is proportional to maximum particle size except that the <250 μm material was processed from two different types of bone with the <250 μm knuckle bone sample dissolving more rapidly than the <250 μm long bone sample and actually crossing over the <150 μm sample at about 10 minutes.

Figure 5:
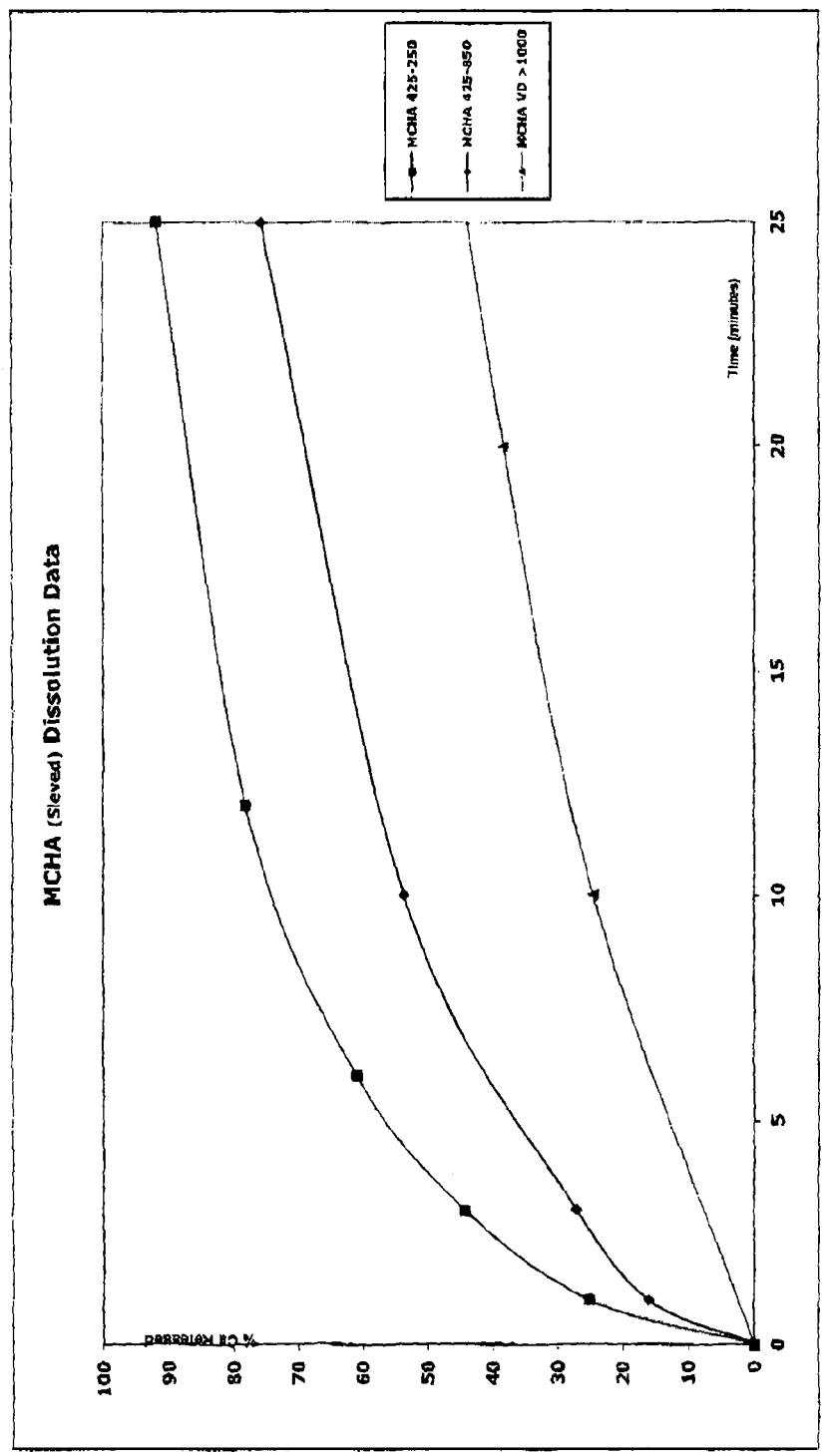
FIG. 5 is shows the effect of sieving on dissolution rate.

FIG. 5 shows the in vitro dissolution from the product sieved to give a more defined particle size distribution. The graph demonstrates that product having a 425-250 μm distribution dissolves more rapidly than a product having a 425-850 μm distribution whereas a product sieved to have particles >1000 μm dissolves the most slowly. As will be demonstrated below, controlling the particle size distribution can have significant in vivo results.

Unlike calcium carbonate or calcium citrate, MCHA is a product with a complex micro-structure and significant protein content. Because of the gentle manufacturing conditions the protein component contains a significant level of bone growth factors, particularly osteocalcin. The following table shows the growth factor content of the inventive MHCA as compared to a conventional hydroxyapatite product known as OHC.

|  | Inventive MHCA (ug/g powder) | Content in OHC (ug/g powder) |
|---|---|---|
| IGF1 | 0.285 | 0.202 |
| IGF2 | 0.17 | 0.101 |
| TGFβ | 0.0275 | 0.025 |
| Osteocalcin | 604 | 7.015 |

Although the inventive MHCA has more of all the growth factors the difference in osteocalcin content is particularly striking being almost two orders of magnitude greater than the conventional product. Those of ordinary skill in the art will understand that osteocalcin is an extremely important bone growth factor. It is secreted only by the osteoblast cells and its presence is well correlated with the process of bone formation. As has been alluded to earlier normal bone activity represents a balance of bone formation and bone resorption. Living bone is constantly remodeled as the osteoclast cells resorb and demineralize bone and the osteoblast cells create new bone matrix proteins and promote their mineralization.

The presence of high levels of osteocalcin in the inventive MHCA is at least a partial explanation of the results obtained when the MHCA is used in a three dimensional gel matrix to promote the differentiation of embedded bone progenitor cells. In contrast to other materials, the MHCA gel suppressed proliferation of both osteoblasts and osteoclasts while strongly promoting the differentiation of the osteoblasts to synthesize and mineralize bone matrix. Thus, the inventive MHCA directly promotes bone formation by "pushing" the osteoblasts in that direction. At the same time it indirectly promotes bone by suppressing the formation of bone resorbing osteoclasts. It is believed that the dramatically higher level of growth factors in the current product contribute to its in vivo effectiveness.

The following claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just-described preferred embodiment can be configured without departing from the scope of the invention. The illustrated embodiment has been set forth only for the purposes of example and that should not be taken as limiting the invention. Therefore, it is to be understood that, within the scope of the appended claims, the invention may be practiced other than as specifically described herein.

REFERENCES

Bolland M J., et al (2011) Calcium supplements with or without vitamin D and risk of cardiovascular events: reanalysis of the Women's Health initiative limited access dataset and metaanalysis. Bristish Medical Journal 342: d2040

Bolland M J., at al, (2008) Vascular events in healthy older women receiving calcium supplementation: a randomized controlled trial. British Medical Journal 336:262-266

Castelo-Branco C., et al., *Efficacy of ossein hydroxyapatite complex with calcium carbonate to prevent bone loss: a meta analysis*. Menopause 16(5) 984-991.

Deroisy R. et al., (1997). Acute changes in serum calcium and parathyroid hormone circulating levels induced by the oral intake of five currently available calcium salts in healthy male volunteers. Clinical Rheumatology, 16: No 3: 249-253

Michaelsson K., et al. (2013) Long term calcium intake and rates of all cause and cardiovascular mortality: community prospective longitudinal cohort study. British Medical Journal; 346:f228

Pelayo I., at al (2008) *Raloxifene plus ossein-hydroxyapatite compound versus raloxifene plus calcium carbonate to control bone loss in postmenopausal women: a randomized trial*. Menopause 15 (6):

Reid I R., (1986) The acute biochemical effects of four proprietary calcium prepartions. Aust N Z J Med. 16:193-197

Ruegsegger P., et al (1995) *Comparison of the treatment effects of ossein-hydroxyapatite compound and calcium carbonate in osteoporotic females. Osteoporosis international* 5: 30-34

Sambrook P N., et al (2011) Does increased sunlight exposure work as a strategy to improve vitamin D status in the elderly: a cluster randomized controlled trial. Osteoporosis International DOI 10.1007/s00198-011-1590-5.

Stepan J J., et 8141991) *Quantitation of growth factors in ossein-mineral-compound. Life Sciences*, 49: PL79-PL84

U.S. Pat. No. 4,919,931 Apr. 24, 1990. Method for producing ossein hydroxyapatite compound. Inventors: Rosenberg nee Goldner Assignee: Robapharm AG (CH)

U.S. Pat. No. 7,029,703, Apr. 18, 2006. Composition for promoting healthy bone structure. Inventors: Krumhar; Johnson. Assignee: Metagenics Inc.

What is claimed is:

1. A method for producing a high osteocalcin microcrystalline hydroxyapatite preparation without using organic solvents to remove fat comprising the steps of:
   selecting bovine leg bone diaphysis;
   reducing the bovine leg bone diaphysis to a predetermined particle size;
   digesting the reduced bovine leg bone diaphysis with a protease under temperature controlled conditions, thereby removing fat while avoiding denaturing growth factors;
   drying the digested bovine leg bone diaphysis; and
   milling the digested bovine leg bone diaphysis to produce high osteocalcin microcrystalline hydroxyapatite with a predetermined particle size distribution, wherein the high osteocalcin microcrystalline hydroxyapatite does not cause elevation of ionized blood calcium levels when administered as a dietary supplement, wherein the high osteocalcin microcrystalline hydroxyapatite preparation has 24-28% protein; and wherein
   the step of digesting takes place at 60° C.-70° C. and the step of digesting includes a step of adjusting the pH to 8.5-8.7.

2. The method according to claim 1, wherein the protease is alcalase.

3. The method according to claim 1, wherein the step of drying is carried out by freeze drying or by low temperature vacuum drying.

4. The method according to claim 1, wherein the step of milling includes sieving said high osteocalcin microcrystalline hydroxyapatite.

5. The method according to claim 1, wherein milling provides a particle size distribution having not more than 30% by weight of the particles having a particle size smaller than 250 micron.

6. The method according to claim 1, wherein milling provides a particle size distribution having not less than 90% by weight of the particles having a particle size smaller than 850 micron.

7. The method according to claim 1, wherein milling provides a particle size distribution having not more than 30% by weight of the particles having a particle size smaller than 250 micron and not less than 90% by weight of the particles having a particle size smaller than 850 micron.

8. The method according to claim 1, said method providing the high osteocalcin microcrystalline hydroxyapatite preparation having 60 to 72% Calcium Hydroxyapatite.

9. The method according to claim 8, said method providing the high osteocalcin microcrystalline hydroxyapatite preparation having less than 5% loss of moisture on drying, less than 1.5% Fat, 65 to 75% Ash residue on ignition, 25 to 29% Calcium (Ca), and 10 to 13% Phosphorus (P).

10. The method according to claim 1, wherein less than 70% of the calcium ion is released after 2.5 minutes of in vitro dissolution testing of the high osteocalcin microcrystalline hydroxyapatite preparation in 0.1 M HCl stirred at 150 RPM at 37±0.5° C.

11. The method according to claim 1, wherein less than 75% of the calcium ion is released after 5 minutes of in vitro dissolution testing of the high osteocalcin microcrystalline hydroxyapatite preparation in 0.1 M HCl stirred at 150 RPM at 37±0.5° C.

12. A method for producing a high osteocalcin microcrystalline hydroxyapatite preparation without using organic solvents to remove fat consisting essentially of the steps of:
  selecting bovine leg bone diaphysis;
  reducing the bovine leg bone diaphysis to a predetermined particle size;
  digesting the reduced bovine leg bone diaphysis with a protease under temperature controlled conditions, thereby removing fat;
  drying the digested bovine leg bone diaphysis; and
  milling the digested bovine leg bone diaphysis to produce high osteocalcin microcrystalline hydroxyapatite with a predetermined particle size distribution, wherein the high osteocalcin microcrystalline hydroxyapatite does not cause elevation of ionized blood calcium levels when administered as a dietary supplement, wherein the high osteocalcin microcrystalline hydroxyapatite preparation has 24-28% protein; and wherein
  the step of digesting takes place at 60° C.-70° C. and the step of digesting includes a step of adjusting the pH to 8.5-8.7.

* * * * *